(12) United States Patent
Hikichi et al.

(10) Patent No.: US 6,197,571 B1
(45) Date of Patent: Mar. 6, 2001

(54) PROTEIN POLYSACCHARIDE 0041

(75) Inventors: Manabu Hikichi, Kanagawa-ken; Shigenobu Okubo, Ibaraki-ken; Eiji Hiroe, Hyogo-ken, all of (JP)

(73) Assignee: Agaricus Laboratories Co., Ltd., Tokyo (JP)

( * ) Notice: Subject to any disclaimer, the term of this patent is extended or adjusted under 35 U.S.C. 154(b) by 0 days.

(21) Appl. No.: 09/205,100

(22) Filed: Dec. 3, 1998

(30) Foreign Application Priority Data

Jan. 16, 1998 (JP) .................................................. 10-018334

(51) Int. Cl.[7] ............................. A01N 63/00; C12N 1/00; C12N 1/02; C12N 1/16; C12P 21/04
(52) U.S. Cl. .................... 435/254.1; 424/93.5; 435/71.1; 435/72; 435/256.8; 435/261; 435/911
(58) Field of Search ................................ 424/93.5, 93.51; 435/254.1, 255.1, 256.8, 911, 71.1, 72, 261

(56) References Cited

U.S. PATENT DOCUMENTS 6,093,694 * 7/2000 Fujimiya et al. ..................... 514/8

FOREIGN PATENT DOCUMENTS

WO98/27992 * 7/1998 (WO) .

OTHER PUBLICATIONS

Patent Abstracts of Japan; Pub. No. 02078630; Inventor: Nakamura Takuji; Date Feb 19, 1990.

Patent Abstracts of Japan; Pub. No. 02211847; Inventor: I to Hitoshi; Date Aug. 23, 1990.

* cited by examiner

Primary Examiner—Leon B. Lankford, Jr.
Assistant Examiner—Deborah K. Ware
(74) Attorney, Agent, or Firm—Browdy and Neimark

(57) ABSTRACT

The present invention relates to preparation of protein polysaccharide 0041 obtained by extracting a dried product of cultured mycelia of *Agaricus blazei* Murrill 0041 with hot water, and protein polysaccharide 0041 shows immunopotentiating antitumor activity when administered, so that it is useful as an antitumor agent against various tumors, and as an immunopotentiating substance against other diseases.

3 Claims, 3 Drawing Sheets

PROTEIN POLYSACCHARIDE 0041

BACKGROUND OF THE INVENTION

1. Field of the Invention

The present invention relates to protein polysaccharide 0041 with an immunopotentiating antitumor activity.

According to the present invention, protein polysaccharide 0041 has an immunopotentiating antitumor activity and thus high potency as an antitumor agent and an immunopotentiating substance for various tumors.

2. Description of the Related Art

Conventionally, fruit body of *Agaricus blazei* is regenerated and manufactured by artificially culturing its mycelia, and its dried fruit body is commercialized in a large amount as functional food.

The water extract of the dried fruit body, extracted with hot water, is drunk with the expectation of efficacy such as immunopotentiation.

Preparation of the fruit body of *Agaricus blazei* requires a considerable day and time for regeneration of the fruit body from seed culture of the mycelia, and the productivity is low and its price for commercialization is consequently high.

There are a large number of *Agaricus blazei* mutants, and their efficacies of the biological activities are rather diverse and generally not uniform as a whole.

The object of the present invention is to search cultured mycelia of *Agaricus blazei*, not for the generation of the fruit body, but for a new strain of *Agaricus blazei* excellent in efficacy and stable productivity and to isolate a new immunopotentiating substance from the cultured mycelia.

SUMMARY OF THE INVENTION

The present invention provides a biologically pure culture of *Agaricus blazei* strain FERM BP-6210 and a method of producing a protein polysaccharide from this strain.

The present invention further provides a protein polysaccharide 0041 produced by this *Agaricus blazei* strain FERM BP-6210.

DETAILED DESCRIPTION OF THE INVENTION

Figure 1:
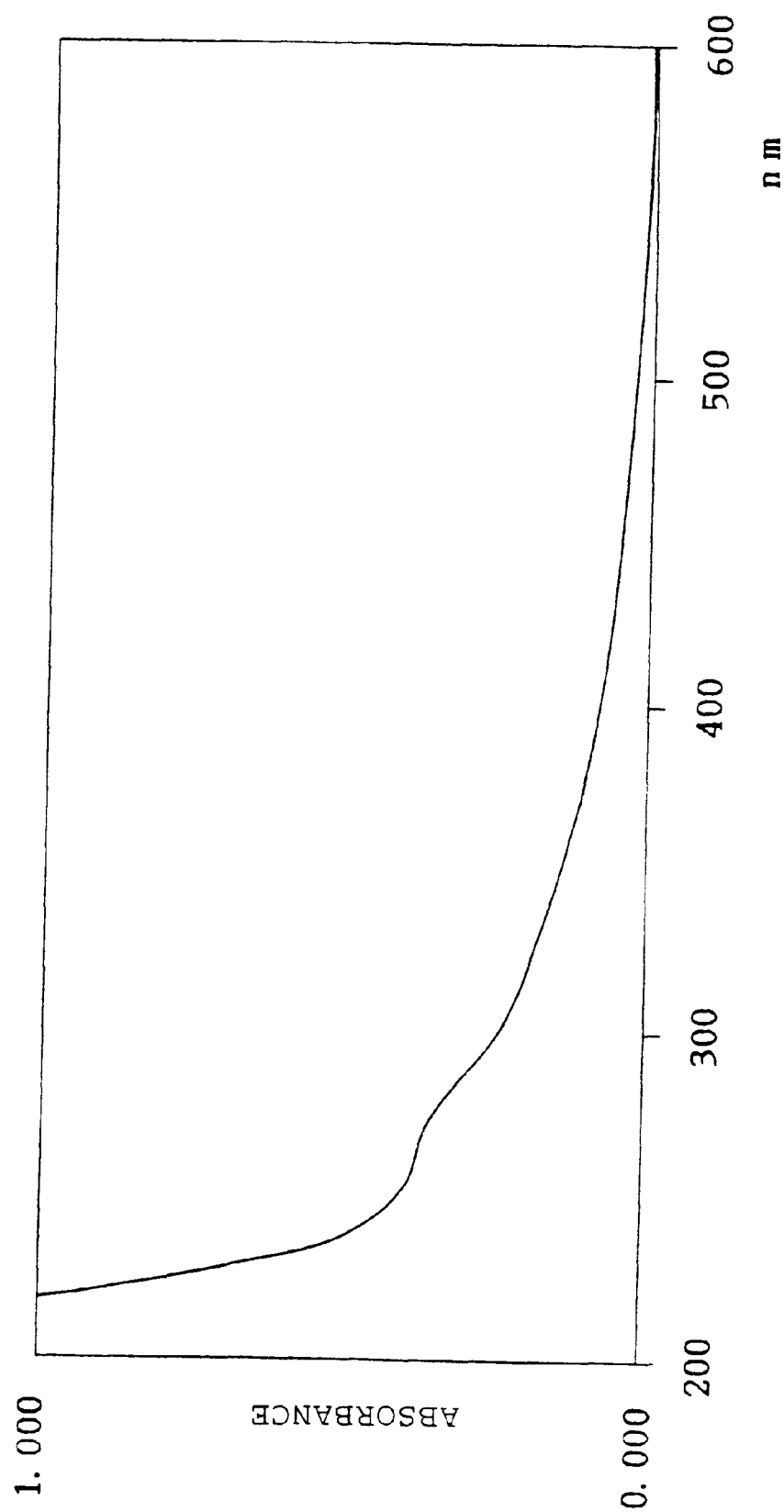
FIG. 1 shows an ultraviolet absorption spectrum of protein polysaccharide 0041.

The present inventors had isolated a large number of the strains with significantly-growing mycelia derived from many fruit bodies of *Agaricus blazei* cultivated at the place of origin in Brazil, then cultured each of them in a liquid medium, extracted the resulting mycelia with hot water, and examined the isolated substances for antitumor activity. As a result, the inventors recognized that only a certain strain has an immunopotentiating antitumor activity superior to that of other strains, thereby have performed the present invention.

In the present invention, the strain was designated *Agaricus blazei* Murrill 0041, and the substance with an immunopotentiating antitumor activity, prepared by the strain, was named protein polysaccharide 0041.

*Agaricus blazei* Murrill 0041 was deposited under accession number FERM BP-6210 on December 18, 1997 with the National Institute of Bioscience and Human-Technology, Agency of Industrial Science and Technology, Japan in accordance with the Budapest Treaty on the International Recognition of the Deposit of Microorganisms for the Purposes of Patent Procedure.

The microbial properties of *Agaricus blazei* Murrill 0041 are as follows:

1. It grows well in MY agar medium (30 g malt extract, 5 g yeast extract, 9 g agar, 1000 ml distilled water) at 27° C. The mycelia are white, grow densely, and are cream-colored when viewed through the cover of a Petri dish. The mycelia elongate radially, and some mycelia branch in two directions to elongate in a dendritic form, unlike the growth of di-nuclear hypha of a basidiomycete such as "shiitake" (Lentinula edodes) which elongate to form clump connections. In long-term culture, rhizomorph of the mycelia are partially formed, fruit bodies are not formed in the Petri dish, and asexual spores are not observed.
2. It grows well in a potato/glucose agar medium as well and exhibits the same properties as in above 1.
3. Its mycelia grow well in shaking culture at 27° C. in a liquid medium (50 g glucose, 5 g yeast extract, 30 g malt extract, adjusted to 1 liter with distilled water), and protein poly-saccharide 0041 is formed in a large amount in the mycelia.

*Agaricus blazei* Murrill 0041 is cultured for production of the mycelia.

Although culture of the mycelia may be carried out in either a solid or liquid medium, the cultivation in a liquid medium is more favorable for treatment of mycelia and is generally used.

The liquid medium may be any liquid media which are utilyzed for cultivation of the mycelia of the basidiomycota.

The medium for shaking culture is preferably a liquid medium prepared by mixing glucose (50 g/L), yeast extract (5.0 g/L), malt extract (30 g/L) and distilled water, and then adjusting the mixture to 1 liter volume with distilled water.

Culture is carried out aerobically in shaking culture, or under stirring and aeration, at about 27° C. for 10 to 14 days, and the mycelia grow satisfactorily.

The cultured mycelia in the liquid medium are filtered under reduced pressure and then pressed in a filter press machine to give wet mycelia. The wet mycelia are dried in hot air to give dried mycelia.

The resulting dried mycelia are moved into a vessel and then mixed with distilled water which is 10 times the dried mycelia in volume, and refluxed for about 1 hour.

The obtained aqueous solution is subjected to press-filtration, and then further clarified by filtration using celite, followed by ultrafiltration treatment to remove low-molecular substances. The obtained retentate is concentrated to an about ½ to about 1/10 volume under reduced pressure, and the concentrate is mixed with a sufficient amount of ethanol and then allowed to stand overnight at room temperature to give a pale-brown precipitate. This precipitate is dried in hot air to give pale-brown powder of protein polysaccharide 0041.

The physicochemical properties of protein polysaccharide 0041 are as follows:

1. It is a protein polysaccharide.
2. The main saccharides of the polysaccharide are glucose and mannose.
3. It turns dark brown in phenol sulfate reaction which indicates 52.8% of saccharide content.

Figure 2:
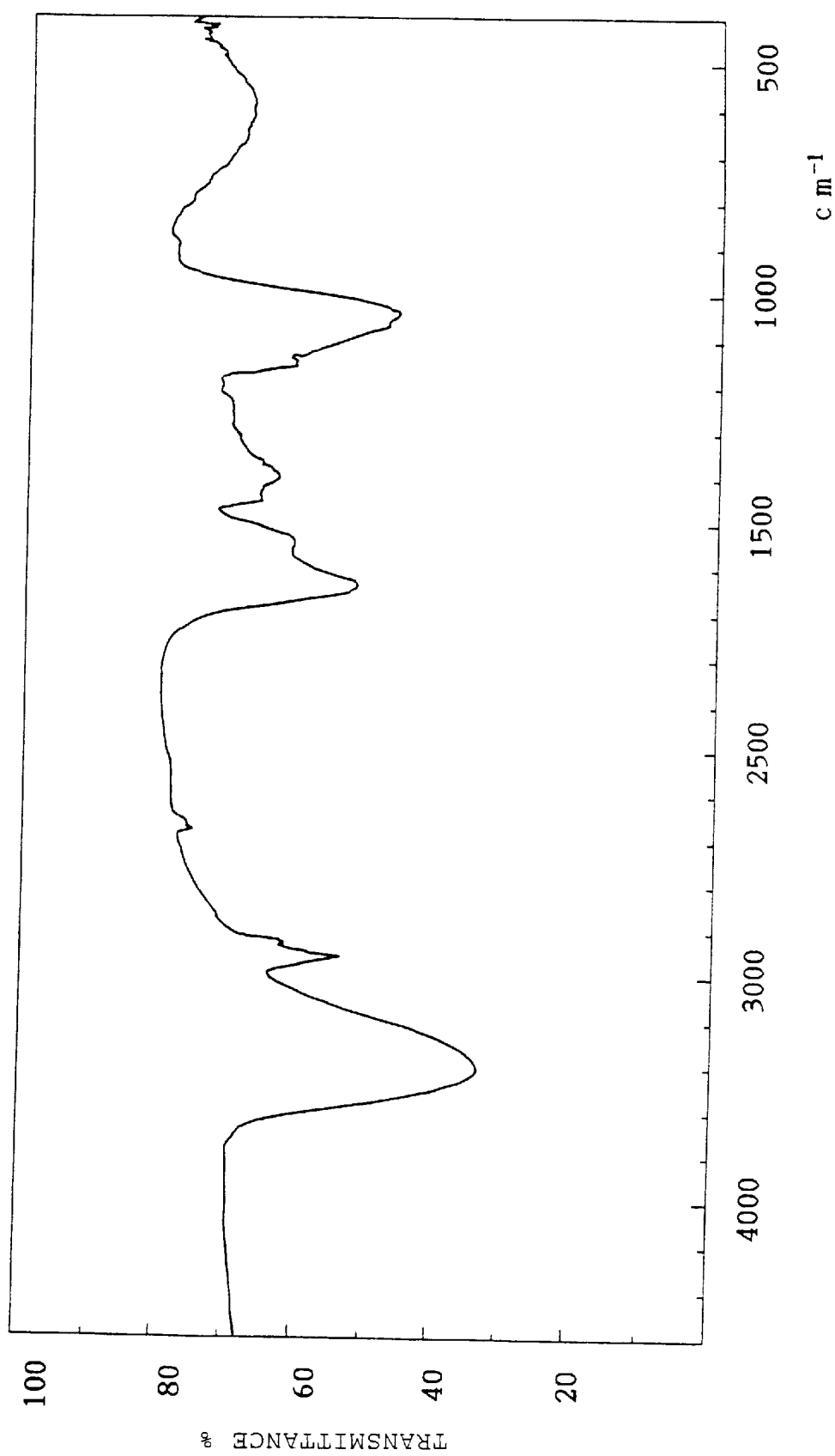
FIG. 2 shows an infrared absorption spectrum of protein polysaccharide 0041.
Figure 3:
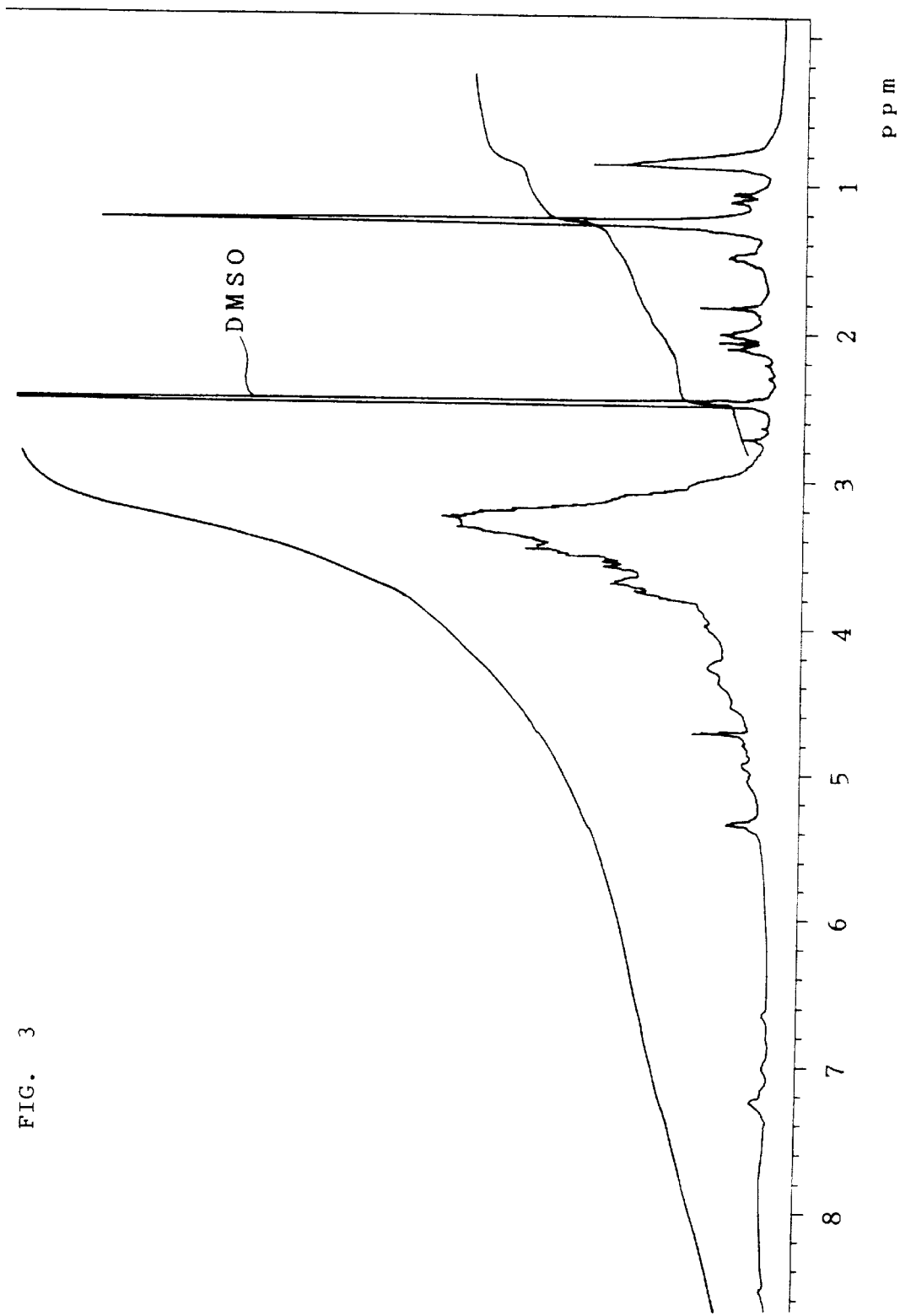
FIG. 3 shows an NMR spectrum of protein polysaccharide 0041.

4. It turns blue in Lowry-Folin reaction to indicate 27.2% of protein content.
5. The amino acid constituents (%) obtained by measuring by an amino acid analyzer the hydrolysates of protein polysaccharide 0041 after hydrolysis with 6 N hydrochloric acid at 110° C. for 12 hours in a sealed tube under reduced pressure are as follows: Asp 10.12, Thr 4.13, Ser 4.85, Glu 13.55, Gly 12.92, Ala 11.55, Val 7.44, Met 2.16, Ile 4.72, Leu 10.94, Tyr 2.68, Phe 3.91, Lys 4.62, His 2.05, Arg 2.40, Cys 0.60, and Pro 1.50.
6. Molecular weight: 85,000 to 105,000, determined by gel filtration chromatography.
7. Melting point: It turns brown at 245° C. and dark brown at 275° C. to 279° C. it decomposes at 275° C. to 279° C.
8. Specific rotation: $[\alpha]_D^{21} = +318°$ (0.33% in water).
9. Solubility: Easily soluble in an aqueous 0.05 N NaOH solution solution and relatively soluble in water, and insoluble in methanol, ethanol, chloroform, benzene and hexane.
10. Color reaction: Positive in phenol/sulfate reaction, biuret reaction, Lowry-Folin reaction, and xanthoprotein reaction.
11. The pH value of the 1.58% aqueous solution is 7.4.
12. The color of its powder is pale-brown.
13. UV absorption spectrum: As shown in FIG. 1.
14. IR absorption spectrum: As shown in FIG. 2.
15. NMR spectrum: As shown in FIG. 3.

Similar to protein polysaccharides obtained from other basidiomycetes, protein polysaccharide 0041 of the present invention is substantially innoxious and shows immunopotentiating antitumor activity in various administrations, so that it is useful as an antitumor agent and can be used as an effective ingredient for the production of an immunopotentiating composition.

The dosage of protein polysaccharide 0041 for oral administration is about 10 mg to about 1000 mg, preferably about 100 mg to about 200 mg/day/person.

EXAMPLES

Example 1
Preparation of Protein Polysaccharide 0041

*Agaricus blazei* Murrill 0041(FERM BP-6210) was cultured in a medium (prepared by dissolving 9 g agar, 30 g malt extract and 5 g yeast extract in distilled water, adjusting the total volume to 1 liter with distilled water, and sterilizing it in an autoclave at 121° C. for 20 min.) in a Petri dish at 26° C. in the dark for 20 days, and the white mycelia, which grew well in a dendritic form, were stamped out with an about 12 mm cork borer to use as the seed culture.

Fifty grams of glucose, 5.0 g of yeast extract, and 30 g of malt extract were added to distilled water to prepare 1 liter liquid medium, and the liquid medium was poured into a 500-ml Sakaguchi flask in a volume of 100 ml/flask and then sterilized at 121° C. for 45 minutes, and the above seed culture was inoculated into each flask and cultured at 27° C. for 10 days. The culture from four flasks containing the cultured mycelia were combined and poured into a 20-liter culture tank (containing 12 liters of the same liquid medium as above) and cultured at 27° C. under aeration at 0.5 vvm with stirring at 50 to 100 rpm for 14 days.

The cultural medium, 12 liters, was filtered under reduced pressure to give the mycelia. The mycelia were then pressed by a filter press machine to give the wet mycelia (water content of 65 to 75%), and the wet mycelia were dried in hot air to give 6.0 g of the dried mycelia.

The dried mycelia were collected, and 50 g thereof was put into a 1000-ml round flask, and 500 ml of distilled water was added thereto. The resultant solution was heated under reflux for 1 hour, then cooled and filtered by press-filtration to give a filtrate, which was further filtered by using celite for clarification.

The clarified filtrate was subjected to ultrafiltration to remove substances of low molecular weights and the obtained retentate was concentrated to 100 ml under reduced pressure.

To 100 ml of the obtained concentrate, was added 400 ml of absolute ethanol. The mixture was allowed to stand overnight at room temperature to give precipitate, which was collected by filtration in vacuo and then dried in hot air whereby 4.8 g of protein polysaccharide 0041 was obtained.

Example 2
Immunopotentiating Antitumor Activity Test

The effect of protein polysaccharide 0041 against sarcoma 180 tumor was examined.

Mice (30 g male ICR) were inoculated with the tumor (0.1 ml subcutaneous inoculation onto the back of a mouse: $3 \times 10^6$ tumor cells). Twenty four hours later, an aqueous solution prepared by dissolving pale-brown protein polysaccharide 0041 obtained in Example 1 in physiological saline (1 mg/ml) was administered intraperitoneally into the mice as one group 10 times for 10 days at a dose of 10 mg/kg/day. Otherwise, physiological saline only was administered into a control group in the test. Twenty days after, i.e., on the day of final dosage, the tumor nodes were removed from the group given the sample and the control group, and the weight of each tumor node was measured. The rate of inhibition is calculated using the following equation:

$$\text{Rate of inhibition } (\%) = (C-T)/C \times 100$$

where T is the average weight of tumor nodes from the group given the sample and C is that from the control group.

The results are as follows:

| Group | Tumor average weight (g) | Degree of tumor inhibition (%) | Complete disappearance |
|---|---|---|---|
| Control group | 12.64 | | 0/10 (Two of ten mice died) |
| Group given protein polysaccharide 0041 | 3.60 | 71.5 | 4/10 |

What is claimed is:
1. A biologically pure culture of *Agaricus blazei* strain FERM BP-6210.
2. A method of producing a protein polysaccharide, comprising:
(1) culturing *Agaricus blazei* strain FERM BP-6210 in a liquid medium;
(2) recovering wet mycelia from the resulting medium;
(3) drying the recovered wet mycelia;
(4) extracting the dried mycelia with hot water to obtain a liquid extract; and
(5) recovering from the liquid extract a protein polysaccharide 0041 having the following physicochemical properties:

(a) the saccharide of the polysaccharide includes glucose and mannose,
(b) molecular weight: 85,000 to 105,000 daltons, as measured by gel filtration chromatography;
(c) said protein polysaccharide 0041 turns brown at 245° C., and turns dark brown when the protein polysaccharide decomposes at 275° C. to 279° C.
(d) specific rotation: $[\alpha]_D^{21}=+318°$ (0.33% in water);
(e) solubility: soluble in aqueous 0.05 N NaOH and water, and insoluble in methanol, ethanol, chloroform, benzene and hexane;
(f) color reaction: positive in phenol/sulfate reaction, biuret reaction, Lowry-Folin reaction, and xanthoprotein reaction;
(g) the pH value of an aqueous solution of 1.58% protein polysaccharide 0041 is 7.4; and
(h) the color of the powder of protein polysaccharide 0041 is pale-brown.

3. Protein polysaccharide 0041 prepared by the method according to claim 2.

* * * * *